United States Patent [19]
Cuppoletti

[11] Patent Number: 6,159,968
[45] Date of Patent: Dec. 12, 2000

[54] ACTIVATION OF CHLORIDE CHANNELS FOR CORRECTION OF DEFECTIVE CHLORIDE TRANSPORT

[75] Inventor: John Cuppoletti, Cincinnati, Ohio

[73] Assignee: University of Cincinnati, Cincinnati, Ohio

[21] Appl. No.: 09/231,760

[22] Filed: Jan. 15, 1999

Related U.S. Application Data

[60] Provisional application No. 60/071,549, Jan. 15, 1998.

[51] Int. Cl.[7] .................. A61K 31/535; A61K 31/445
[52] U.S. Cl. .............. 514/234.5; 514/253; 514/318; 514/338
[58] Field of Search ................... 514/234.5, 253, 514/318, 338

[56] References Cited

U.S. PATENT DOCUMENTS

| | | | |
|---|---|---|---|
| 4,255,431 | 3/1981 | Junggren et al. | 424/263 |
| 5,066,652 | 11/1991 | Chiesi et al. | 514/235.8 |
| 5,250,527 | 10/1993 | Ife | 514/234.5 |
| 5,518,730 | 5/1996 | Fuisz | 424/426 |
| 5,576,338 | 11/1996 | Friesen et al. | 514/337 |
| 5,603,943 | 2/1997 | Yanagawa | 424/434 |
| 5,607,691 | 3/1997 | Hale et al. | 424/449 |

OTHER PUBLICATIONS

Starlinger et al. *American Journal of Physiology* Jan. 1986, 250(1, Pt. 1), G118–G126.
Takeguchi et al. *The Journal of Biological Chemistry* Feb. 25, 1986, 261(6), 2560–2566.

*Primary Examiner*—Kathleen K. Fonda
*Attorney, Agent, or Firm*—Frost & Jacobs LLP

[57] ABSTRACT

This invention provides a method for increasing the permeability of epithelial cells to a chloride ion in a subject comprising administering a permeability enhancing amount of a composition comprising a specifically-defined nontoxic, benzimidazole or benzimidazole derivative. The invention also relates to a method of treating cystic fibrosis comprising administering an epithelial cell chloride permeability enhancing amount of a composition comprising a specifically-defined nontoxic, benzimidazole or benzimidazole derivative. The benzimidazole compound having chloride channel activation activity for use in this invention includes a 2-[(pyridyl)-methylsulfinyl or -methylthio] benzimidazole derivatives and salts thereof, for instance. Specifically, these include the compounds omeprazole, lansoprazole, thimoprazole and pantoprazole. When appropriately applied, these compounds can correct detective chloride transport, increasing the salt and water flux in diseased tissues to levels closer to those of normal tissues thus reducing life-threatening complications.

11 Claims, No Drawings

ACTIVATION OF CHLORIDE CHANNELS FOR CORRECTION OF DEFECTIVE CHLORIDE TRANSPORT

This application claims priority under 35 U.S.C. § 119 (e) to provisional U.S. application Ser. No. 60/071,549, filed Jan. 15, 1998.

The research underlying this invention has been supported by one or more of the following grants: 5 R01DK43377-05, 2R01DK43816-06, 1R01DK50749-01A1, 1R01DK50749-01 and 1R01HL57614-01, awarded by the National Institutes of Health; and CUPPOL96PO, awarded by the Cystic Fibrosis Foundation ("CFF"). This application is based on U.S. Provisional Application Ser. No. 60/071,549, filed Jan. 15, 1998.

BACKGROUND OF THE INVENTION

This invention relates generally to medical treatment methods. Specifically, the invention relates to methodology for the correction of defective chloride transport by increasing the salt and water flux in diseased tissues to levels closer to those found in normal tissues.

The invention discloses a method of activation of chloride transport in cystic fibrosis. Specifically, the methods of the present invention rely on the ability of benzimidazoles, e.g., omeprazole (PRILOSEC™), to increase the activity of alternate chloride transport proteins in the lung. Omeprazole, a drug currently used for treatment of gastric ulcers, is known to function as a proton pump inhibitor ("PPI"). The present invention discloses that 2 it is also capable of activating chloride transport proteins on the surface of lung epithelial cells.

This treatment will reduce life-threatening complications frequently found in diseases such as cystic fibrosis. The method of increasing the permeability of epithelial cells to chloride ions comprises administering to a patient in need of such treatment a permeability enhancing amount of a composition comprising a specifically-defined nontoxic, benzimidazoles and benzimidazole derivatives.

Cystic fibrosis is a lethal disease affecting approximately one in 2,500 live Caucasian births and is the most common autosomal recessive disease in Caucasians. Patients with this disease have reduced chloride ion permeability in the secretory and absorptive cells of organs with epithelial cell linings, including the airways, pancreas, intestine, sweat glands and male genital tract. This, in turn, reduces the transport of water across the epithelia. The lungs and the GI tract are the predominant organ systems affected in this disease and the pathology is characterized by blocking of the respiratory and GI tracts with viscous mucus. The chloride impermeability in affected tissues is due to mutations in a specific chloride channel, the cystic fibrosis transmembrane conductance regulator protein (CFTR), which prevents normal passage of chloride ions through the cell membrane (Welsh et al., *Neuron,* 8:821–829 (1992)). There is no effective treatment for the disease, and therapeutic research is focused on gene therapy and/or activating the defective or other chloride channels in the cell membrane to normalize chloride permeability (Tizzano et al., *J. Pediat.,* 120:337–349 (1992)). Damage to the lungs due to mucus blockage, frequent bacterial infections and inflammation is the primary cause of morbidity and mortality in CF patients and, although maintenance therapy has improved the quality of patients' lives, the median age at death is still only around 30 years.

The thick build-up of mucus deposits in the lungs leads to a higher than normal susceptibility towards fatal pulmonary infections. It is these infections, often of the Pseudomonas aeruginosa type, that are generally the causative agents of cystic fibrosis related death. At present, the established treatment protocols for cystic fibrosis involve treating these secondary infections with appropriate antibiotics, as well as adjusting diet and removing by physical means the deleterious build up of mucociliary secretions. Thus, considerable current effort is being devoted to developing treatments that operate by attacking the underlying cause of disease. Here, a variety of approaches have been explored. These range from attempts at gene therapy (incorporating the normal, wild-type cystic fibrosis gene into epithelia cells) to the administration of agents that restore electrolyte balance either by opening up other non-CFTR dependent chloride anion channels or by inhibiting cellular uptake of sodium cations. Unfortunately, the viability of this latter electrolyte balance restoration approach still remains limited.

The activation of the defective and/or alternative functioning chloride channels in cystic fibrosis epithelial cells in order to normalize their permeability to chloride is one of the primary therapeutic goals of the treatment of cystic fibrosis and has not yet been accomplished (Boat, T. F., Welsh, M. J. and Beaudet, A. L., "Cystic Fibrosis" in *The Metabolic Basis of Inherited Disease,* pp. 2649–2680 (Striver, C. R., Beaudet, A. L., Sly, W. S. and Valle, D. eds.) McGraw-Hill, New York (1989)). Thus, there exists an urgent need for a treatment that increases the permeability of epithelial cells to chloride and thereby can be used to treat cystic fibrosis. Such a treatment would be most beneficial if it were nontoxic and nonirritating to the epithelial cell linings, yet allowed the restoration of the proper chloride equilibrium of the cells, as well as the clearing of existing mucus. The present invention satisfies this need by providing methods and compounds which can therapeutically relieve both the cause of the manifestations of cystic fibrosis, as well as the manifestations themselves.

Patents which discuss the use of benzimidazoles and benzimidazole derivative molecules include the following:

U.S. Pat. No. 5,607,69 1, Hale et al., issued Mar. 4, 1997, discloses methods of delivering pharmaceutical agents across membranes, including the skin layer or mucosal membranes of a patient. A pharmaceutical agent is covalently bonded to a chemical modifier, via a physiologically cleavable bond, such that the membrane transport and delivery of the agent is enhanced.

U.S. Pat. No. 5,576,338 Friesen et al., issued Nov. 19, 1996, describes bis(biaryl) compounds having activity as leukotriene biosynthesis inhibitors, to methods for their preparation, and to methods and pharmaceutical formulations for using these compounds in mammals (especially humans). Because of their activity as leukotriene biosynthesis inhibitors, the compounds are useful as anti-asthmatic, anti-allergic, anti-inflammatory, and cytoprotective agents including treatment of chronic lung diseases such as cystic fibrosis, bronchitis and other small- and large-airway diseases.

U.S. Pat. No. 5,603,943, Yanagawa, issued Feb. 18, 1997, discloses nasally administrable compositions comprising a physiologically active substance having a molecular weight of not more than 40,000 and a physiologically acceptable powdery or crystalline polyvalent metal carrier, wherein a physiologically effective amount of said active substance is dispersed homogeneously in and adsorbed homogeneously onto the metal carrier. Among the hundreds of actives disclosed is omeprazole.

U.S. Pat. No. 5,518,730, Fuisz, issued May 21, 1996, discloses biodegradable controlled release delivery systems using melt-spun biodegradable polymers as carriers for bio-effecting agents such as pharmaceutical actives. Non-limiting examples of specific bio-effecting agents which may be useful in the present invention includes omeprazole.

U.S. Pat. No. 5,066,652, Chiesi et al., issued Nov. 19, 1991, discloses a new class of inhibitors of gastric acidity consisting of benzimidazole derivatives of omeprazole. Pharmaceutical compositions of the invention can be administered by inhalatory or buccal routes, in any administration form. Inhalatory compositions can be solutions, suspensions, emulsions or powders of the active ingredient to be administered through an aerosol, or to be conditioned in aerosol bombs.

U.S. Pat. No. 5,250,527, Ife, issued Oct. 5, 1993, relates to the novel substituted benzimidazole derivatives and intermediates, which are inhibitors of potassium stimulated H+-K+ ATPase activity, the pharmaceutical compositions containing them and a method of inhibiting gastric acid secretion by administering them. A typical composition for inhalation comprises a solution, suspension or emulsion that may be administered in the form of an aerosol using a conventional propellant such as dichlorodifluoromethane or trichlorofluoromethane.

U.S. Pat. No. 4,255,431, Junggren et al., issued Mar. 10, 1981, is the original omeprazole patent which relates to compounds having valuable properties in affecting gastric acid secretion.

SUMMARY OF THE INVENTION

Cystic fibrosis is characterized by defects in salt and water transport in a variety of epithelial tissues. The basis of the defect is the gene product termed the cystic fibrosis trans-membrane regulator protein (CFTR). The CFTR has been shown to be a chloride channel. The present invention relates to a method of increasing the permeability of epithelial cells to chloride ions in a subject, for example, in treating cystic fibrosis, comprising administering a permeability enhancing amount of a composition comprising a specifically-defined nontoxic, benzimidazole or benzimidazole derivative.

The benzimidazole compound having chloride channel activation activity for use in this invention includes a 2-[(pyridyl)-methylsulfinyl or -methylthio]benzimidazole derivatives and salts thereof, for instance. Specifically, these include the compounds omeprazole, lansoprazole, thimoprazole and pantoprazole. The preferred are compounds are represented by the formula (I):

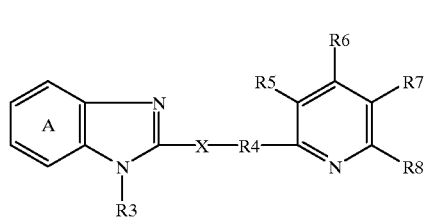

wherein ring A may optionally be substituted; R3 is hydrogen, alkyl, acyl, carbalkoxy, carbamoyl, alkylcarbamoyl, dialkylcarbamoyl or alkylsulfonyl; R5, R7 and R8 are the same or different, hydrogen, alkyl, alkoxy or alkoxyalkoxy; R6 is hydrogen, alkyl or a group of the formula —OR6 in which R6 is a hydrocarbon group which may optionally be substituted.

Referring to the above formula (I), the substituent that may optionally be present on ring A includes halogen, alkyl which may be substituted, cycloalkyl which may be substituted, alkenyl which may be substituted, alkoxy which may be substituted, cyano, carboxy, carbalkoxy, carbalkoxyalkyl, carbamoyl, carbamoylalkyl, hydroxy, hydroxyalkyl, acyl, carbamoyloxy, nitro, acyloxy, aryl, aryloxy, alkylthio and alkylsulfinyl, among others.

When appropriately applied, these compounds can correct detective chloride transport, increasing the salt and water flux in diseased tissues to levels closer to those of normal tissues thus reducing life-threatening complications. In the methods of the present invention, a safe and effective amount, preferably from about 1 to about 200 mg, of a benzimidazole compound as defined above is administered to a patient in need of such treatment. The compositions useful for such treatment include a safe and effective amount, preferably from about 0.001% to about 10% (w/w), of the benzimidazole derivative together with, preferably from about 10% to about 99% (w/w), of a pharmaceutically-acceptable carrier. Methods of application will differ, depending on the affected tissue; however, one appropriate method would be the use of liquid aerosols, particulates or sprays. These compounds are of low molecular weight and relatively stable. Members of the general class to which these compounds belong have found use in other applications, and some members of this class are derived from natural products. These compounds should be much less expensive than proteins and recombinant DNA products, which are currently being tested as therapeutic agents for cystic fibrosis. In contrast to other agents, such as amiloride and nucleotides, which act indirectly on certain macromolecules expressed in lung tissues, these compounds do not require the presence of such other substances. Thus, these compounds increase the permeability of any tissue with which they come in contact. There are pathological conditions and disease states other than cystic fibrosis that might also benefit from treatment with compounds that increase salt and water permeability. These include brain swelling, renal disease, and heart disease.

DETAILED DESCRIPTION OF THE INVENTION

As used herein, "a safe and effective amount" of a composition is that amount which is pharmaceutically safe to a subject and that causes the epithelial cell membrane to allow the activation of chloride channels while causing no or an acceptable level of side effects.

The benzimidazole compound having chloride channel activation activity for use in this invention includes a 2-[(pyridyl)-methylsulfinyl or -methylthio]benzimidazole derivatives and salts thereof, for instance. Specifically, these include the compounds omeprazole, lansoprazole, thimoprazole and pantoprazole. The preferred are compounds are represented by the formula (I):

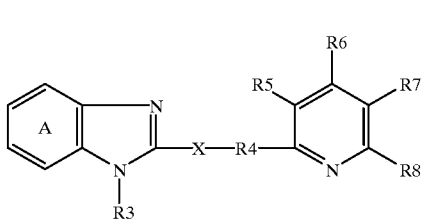

wherein ring A may optionally be substituted; R3 is hydrogen, alkyl, acyl, carbalkoxy, carbamoyl, alkylcarbamoyl, dialkylcarbamoyl or alkylsulfonyl; R5, R7 and R8 are, the same or different, hydrogen, alkyl, alkoxy or alkoxyalkoxy; R6 is hydrogen, alkyl or a group of the formula —OR8 in which R8 is a hydrocarbon group which may optionally be substituted.

These compounds are described in, for example, U.S. Pat. No. 4,045,563, U.S. Pat. No. 4,255,431, U.S. Pat. No. 4,359,465, U.S. Pat. No. 4,472,409, U.S. Pat. No. 4,508,905, EP-A-59 181277, U.S. Pat. No. 4,628,098, U.S. Pat. No. 4,738,975, U.S. Pat. No. 5,045,321, U.S. Pat. No. 4,786,505, U.S. Pat. No. 4,852,230, U.S. Pat. No. 4,769,456, U.S. Pat. No. 5,045,552, EP-A-295603, U.S. Pat. No. 5,312,824, EP-A-166287, EP-A-519365, U.S. Pat. No. 5,635,520, etc., which are incorporated herein by reference.

Referring to the above formula (I), the substituent that may optionally be present on ring A includes halogen, alkyl which may be substituted, cycloalkyl which may be substituted, alkenyl which may be substituted, alkoxy which may be substituted, cyano, carboxy, carbalkoxy, carbalkoxyalkyl, carbamoyl, carbamoylalkyl, hydroxy, hydroxyalkyl, acyl, carbamoyloxy, nitro, acyloxy, aryl, aryloxy, alkylthio and alkylsulfinyl, among others.

The respective substituent groups are now specifically described.

The halogen may for example be fluorine, chlorine, bromine or iodine. The preferred are fluorine and chlorine. The most preferable is fluorine.

The alkyl group for the alkyl which may be substituted includes straight-chain or branched C 1–10 alkyl groups (e.g. methyl, ethyl, n-propyl, isopropyl, n-butyl, isobutyl, sec-butyl, tert-butyl, n-pentyl, iso-pentyl, neopentyl, hexyl, heptyl, octyl, nonyl and decyl, among others). The preferred are straight-chain or branched C 1–6 alkyl groups. The still more advantageous are straight-chain or branched C 1–3 alkyl groups. The substituent on the substituted alkyl includes halogen, nitro, cyano, hydroxy, carboxy, amidino, guanidino and carbamoyl, amino which may be mono- or di-substituted by alkyl, acyl, etc., among others.

The cycloalkyl group for the cycloalkyl which may be substituted includes C 3–7 cycloalkyl groups. Examples of such cycloalkyl are cyclopropyl, cyclobutyl, cyclopentyl, cyclohexyl and cycloheptyl. Such cycloalkyl groups may each be substituted by, for example, halogen, nitro, cyano, hydroxy, carboxy, amidino, guanidino and carbamoyl, amino which may be mono- or di-substituted by alkyl, acyl, etc., among others.

The alkenyl group for the alkenyl which may be substituted includes straight-chain or branched C 2–16 alkenyl groups. The preferred alkenyl group includes allyl, vinyl, crotyl, 2-penten-1-yl, 3-penten-1-yl, 2-hexen-1-yl, 3-hexen-1-yl, 2-methyl-2-propen-1-yl and 3-methyl-2-buten-1-yl, among others. The further preferred are straight-chain or branched C 2–6 alkenyl groups. The still more advantageous are straight-chain or branched C 2–4 alkenyl groups. Such alkenyl groups may have substituents, such as halogen, nitro, cyano, amidino, guanidino, amino which may be mono- or di-substituted by alkyl, acyl, etc., and so on.

The alkenyl groups mentioned above include isomers (E- and Z-forms) with respect to the double bond.

The alkoxy group for the alkoxy which may be substituted includes C 1–10 alkoxy groups, among others. As such, the alkoxy group specifically includes methoxy, ethoxy, n-propoxy, isopropoxy, n-butoxy, isobutoxy, sec-butoxy, tert-butoxy, n-pentoxy, isopentoxy, neopentoxy, hexyloxy, heptyloxy, octyloxy, nonyloxy, cyclobutoxy, cyclopentoxy, cyclohexyloxy and so on. The preferred are C 1–6 alkoxy groups. The more advantageous are C 1–3 alkoxy groups. Such alkoxy groups may be substituted, for example, by halogen, nitro, amidino and guanidio, amino which may be mono- or di-substituted by alkyl, acyl, etc., among others.

The halogen which may occur as a substituent on the above alkyl, cycloalkyl, alkenyl or alkoxy group includes chlorine, bromine, fluorine, iodine, and so on.

The alkyl moiety of the alkylamino which may substitute the above alkyl, cycloalkyl, alkenyl or alkoxy group includes straight-chain or branched C 1–6 alkyl groups, among preferred examples. The preferred examples are methyl, ethyl, n-propyl, isopropyl, n-butyl, isobutyl, tert-butyl, sec-butyl, n-pentyl, isopentyl, n-hexyl, isohexyl and so on. Among others, particularly are straight-chain or branched C 1–4 alkyl groups.

The acyl moiety of the acylamino which may substitute the above alkyl, cycloalkyl, alkenyl or alkoxy group includes acyl groups derived from organic carboxylic acids, for instance. The preferred are C 1–6 alkanoyl groups, such as formyl, acetyl, propionyl, butyryl, isobutyryl, valeryl, isovaleryl, pivaloyl, hexanoyl, etc. Particularly C 1–4 alkanoyl groups are preferable.

The number of substituents on the above alkyl, cycloalkyl, alkenyl or alkoxy group may range from 1 to 6, preferably 1 to 3.

The substituted alkyl group specifically includes trifluoromethyl, trifluoroethyl, difluoromethyl, trichloromethyl, hydroxymethyl, 1-hydroxyethyl, 2-hydroxyethyl, methoxyethyl, ethoxyethyl, 1-methoxyethyl, 2-methoxyethyl, 2,2-dimethoxyethyl, 2,2-diethoxyethyl and 2-diethylphosphorylethyl, among others. The preferred are difluoromethyl, trifluoromethyl and hydroxymethyl. The more desirable is trifluoromethyl.

The substituted cycloalkyl group specifically includes 2-aminocyclopropan-1-yl, 4-hydroxycyclopentan-1-yl and 2,2-difluorocyclopentan-1-yl, among others.

The substituted alkenyl group specifically includes 2,2-dichlorovinyl, 3-hydroxy-2-propen-1-yl, 2-methoxyvinyl and so on.

The substituted alkoxy group specifically includes difluoromethoxy, trifluoromethoxy, 2,2,2-trifluoroethoxy, 2-methoxyethoxy, 4-chlorobenzyloxy, 2-(3,4-dimethoxyphenyl)ethoxy and so on. The preferred is difluoromethoxy.

The alkoxy moiety of the carbalkoxy group includes C 1–7 alkoxy groups (e.g methoxy, ethoxy, n-propoxy, isopropoxy, n-butoxy, isobutoxy, sec-butoxy, tert-butoxy, n-pentoxy, isopentoxy, neopentoxy, hexyloxy, heptyloxy, etc.).

The alkoxy moiety of the carbalkoxyalkyl group includes C 1–4 alkoxy groups (e.g. methoxy, ethoxy, n-propoxy, isopropoxy, n-butoxy, isobutoxy, sec-butoxy, tert-butoxy, etc.), among others. The alkyl moiety includes C 1–4 groups (e.g. methyl, ethyl, n-propyl, isopropyl, n-butyl, isobutyl, sec-butyl, tert-butyl, etc.), among others. Specifically, carbomethoxymethyl, 2-carbomethoxyethyl, 2-carbomethoxypropyl, carboethoxymethyl, 2-carboethoxyethyl, 2-carbomethoxypropyl, 2-carbomethoxypropyl, carbopropoxymethyl, carbobutoxymethyl, etc. can be mentioned.

The alkyl moiety of the carbamoylalkyl group includes C 1–4 alkyl groups (e.g. methyl, ethyl, n-p ropyl, isopropyl, n-butyl, isobutyl, sec-butyl, tert-butyl, etc.).

The alkyl moiety of the hydroxyalkyl group includes C 1–7 alkyl groups (e.g. methyl, ethyl, n-propyl, isopropyl, n-butyl, isobutyl, sec-butyl, tert-butyl, n-pentyl, isopentyl, neopentyl, hexyl, heptyl, etc.)

The acyl group and the acyl moiety of the acyloxy group respectively include C 1–4 alkanoyl groups such as formyl, acetyl, propionyl, butyryl, isobutyryl and so on.

The aryl group and the aryl moiety of the aryloxy group respectively include C 6–12 aryl groups (e.g. phenyl, naphthyl, etc.).

The alkyl moiety of the alkylthio or alkylsulfinyl group includes C 1–6 alkyl group (e.g., methyl, ethyl, n-propyl, isopropyl, n-butyl, isobutyl, sec-butyl, tert-butyl, n-pentyl, isopentyl, neopentyl, hexyl, etc.)

The number of substituents on substituted ring A is preferably 1 to 4 and, for still better results, 1 to 2. The positions of such substituents on the benzene ring may for example be 4- and 5-positions. The 5-position is preferred.

The preferred is ring A which may optionally be substituted by i) halogen, ii) alkyl group which may be substituted, iii) cycloalkyl group which may be substituted, iv) alkenyl group which may be substituted or v) alkoxy group which may be substituted.

The alkyl group represented by R3, includes C 1–5 alkyl groups such as methyl, ethyl, n-propyl, isopropyl, n-butyl, isobutyl, sec-butyl, tert-butyl, n-pentyl, isopentyl, neopentyl, etc. The acyl group represented by R3 includes C 1–4 acyl groups such as C 1–4 alkanoyl group etc. The carbalkoxy group represented by R3 includes those having C 1–4 alkoxy groups such as formyl, acetyl, propionyl, butyryl, isobutyryl, etc. The alkylcarbamoyl and dialkylcarbamoyl groups represented by R3 respectively include those having C 1–4 alkyl moieties such as methyl, ethyl, n-propyl, isopropyl, n-butyl, isobutyl, sec-butyl, tert-butyl, etc. The alkylsulfonyl group represented by R3 includes those having C 1–4 alkyl moieties such as those mentioned just above. R3 is preferably hydrogen.

R4 is selected from the group consisting of straight and branched alkylene groups having 1 to 4 carbon atoms, whereby at most one methylene group is present between X and the pyridyl group. Preferably, R4 is $CH_2$.

The alkyl group represented by R5, R7 or R8 includes straight-chain or branched C 1–10 alkyl groups (e.g. methyl, ethyl, n-propyl, isopropyl, n-butyl, isobutyl, sec-butyl, tert-butyl, n-pentyl, isopentyl, neopentyl, hexyl, heptyl, octyl, nonyl, decyl, etc.). Among these alkyl groups, straight-chain or branched C 1–6 alkyl groups to are preferred, and straight-chain or branched C 1–3 alkyl groups are particularly desirable.

The alkoxy group represented by R5, R7 or R8 includes C 1–10 alkoxy groups (e.g. methoxy, ethoxy, n-propoxy, isopropoxy, n-butoxy, isobutoxy, sec-butoxy, tert-butoxy, n-pentoxy, isopentoxy, neopentoxy, hexyloxy, heptyloxy, octyloxy, nonyloxy, etc.). The preferred are C 1–6 alkoxy groups. The more desirable are C 1–3 alkoxy groups.

The alkoxy moiety of the alkoxyalkoxy group represented by R5, R7 or R8 includes C 1–4 alkoxy groups (e.g. methoxy, ethoxy, n-propoxy, isopropoxy, n-butoxy, isobutoxy, sec-butoxy, tert-butoxy, etc.).

R5 is preferably hydrogen, alkyl or alkoxy.

R7 is preferably hydrogen, alkyl or alkoxy.

R8 is preferably hydrogen.

X is selected from the group consisting of S, SO or $SO_2$. X is preferably SO.

The alkyl group represented by R4 includes C 1–4 alkyl groups (e.g. methyl, ethyl, n-propyl, isopropyl, n-butyl, isobutyl, sec-butyl, tert-butyl, etc.).

The hydrocarbon moiety of the hydrocarbon group which may optionally be substituted, represented by R8, is preferably a C 1–3 hydrocarbon group such as C 1–6 straight-chain or branched alkyl groups (e.g. methyl, ethyl, propyl, isopropyl, butyl, isobutyl, sec-butyl, pentyl, isopentyl, hexyl, etc.), C 2–6 alkenyl groups (e.g. vinyl, allyl, 2-butenyl, methylallyl, 3-butenyl, 2-pentenyl, 4-pentenyl, 5-hexenyl, etc.), C 2–6 alkinyl groups (e.g. ethynyl, propargyl, 2-butin-1-yl, 3-butin-2-yl, 1-pentin-3-yl, 3-pentin-1-yl, 4-pentin-2-yl, 3-hexin-1-yl, etc.), C 2–6 cycloalkyl groups (e.g. cyclopropyl, cyclobutyl, cyclopentyl, cyclohexyl, etc.), C 3–6 cycloalkenyl groups (e.g. cyclobutenyl, cyclopentenyl, cyclohexenyl, cyclohexadienyl, etc.), and C 7–13 aralkyl groups (e.g. benzyl, 1-phenethyl, 2-phenethyl, etc.), and C 6–10 aryl groups (e.g. phenyl, naphthyl, etc.), and so on. Among others, straight-chain or branched C 1–6 alkyl groups (e.g. methyl, ethyl, propyl, isopropyl, butyl, isobutyl, sec-butyl, pentyl, isopentyl, hexyl, etc.) are preferred. Particularly, straight-chain or branched C 1–4 alkyl groups are preferred.

The substituent group of the substituted hydrocarbon group includes, among others, C 6–10 aryl groups (e.g. phenyl, naphthyl, etc.), amino, C 1–6 alkylamino (e.g. methylamino, ethylamino, isopropylamino, etc.), di-C 1–6 alkylamino (e.g. dimethylamino, diethylamino, etc.), azide, nitro, halogen (e.g. fluorine, chlorine, bromine and iodine), hydroxy, C 1–4 alkoxy (e.g. methoxy, ethoxy, propoxy, butoxy, etc.), C 6–10 aryloxy (e.g. phenoxy, naphthyloxy, etc.), C 1–6 alkylthio (e.g. methylthio, ethylthio, propylthio, etc.), C 6–10 arylthio (e.g. phenylthio, naphthylthio, etc.), cyano, carbamoyl, carboxy, C 1–4 alkoxycarbonyl (e.g. methoxycarbonyl, ethoxycarbonyl, etc.), C 7–11 aryloxycarbonyl (e.g. phenoxycarbonyl, 1-naphthyloxycarbonyl, $^2$-naphthyloxycarbonyl, etc.), carboxy-C 1–4 alkoxy (e.g. carboxymethoxy, 2-carboxyethoxy, etc.), C 1–6 alkanoyl (e.g. formyl, acetyl, propionyl, isopropionyl, butyryl, pentanoyl, hexanoyl, etc.), C 7–11 aroyl (e.g. benzoyl, 1-naphthoyl, 2-naphthoyl, etc.), C 6–10 arylsulfonyl (e.g. benzenesulfonyl, 1-naphthylsulfonyl, 2-naphthylsulfonyl, etc.), C 1–6 alkylsulfinyl (e.g. methylsulfinyl, ethylsulfinyl, etc.), C 6–10 arylsulfinyl (e.g. benzenesulfinyl, 1-naphthylsulfinyl, 2-naphthylsulfinyl, etc.), C 1–6 alkylsulfonyl (e.g. methylsulfonyl, ethylsulfonyl, etc.), 5- or 6-membered heterocyclic groups having 1 to 4 hetero-atoms (e.g. N, O, S, etc.) (e.g. 2-furyl, 2-thienyl, 4-thiazolyl, 4-imidazolyl, 4-pyridyl, 1,3,4-thiadiazol- 2-yl, 1-methyl-5-tetrazolyl, etc.), 5- or 6-membered heterocyclic carbonyl groups having 1 to 4 hetero-atoms (e.g. N, O, S) (e.g. 2-froyl, 2-thenoyl, nicotinyl, isonicotinyl, etc.) and 5- or 6-membered heterocyclic thio groups having 1 to 4 hetero-atoms (e.g. N, O, S, etc.) (e.g. 4-pyridylthio, 2-pyrimidylthio, 1,3,4-thiadiazol-2-ylthio, 1-methyl-5-tetrazolythio, etc.). The heterocyclic thio groups may each form a bicyclic structure with a benzene ring (e.g. 2-benzothiazolylthio, 8-quinolylthio, etc.). The preferred substituents are halogen (e.g. fluorine, chlorine, bromine and iodine), hydroxy, and C 1–4 alkoxy (e.g. methoxy, ethoxy, propoxy, butoxy, etc.).

The number of such substituents may range from 1 to 5 and is preferably 1 to 3.

R6 is preferably an alkoxy group which may be substituted or an alkoxyalkoxy group which may be substituted. The alkoxy for the alkoxy group which may be substituted includes C 1–8 alkoxy groups (e.g. methoxy, ethoxy, n-propoxy, isopropoxy, n-butoxy, isobutoxy, sec-butoxy, tert-butoxy, n-pentoxy, isopentoxy, neopentoxy, hexyloxy, heptyloxy, octyloxy, etc.). Each of the alkoxy group for the alkoxyalkoxy which may be substituted includes C 1–4 alkoxy groups (e.g. methoxy, ethoxy, n-propoxy, isopropoxy, n-butoxy, isobutoxy, sec-butoxy, tert-butoxy, etc.). R6 is an optionally halogeno C 1–8 alkoxy group, preferably an optionally halogeno C 1–4 alkoxy group, or an optionally halogeno alkoxyalkoxy group. Preferred specific examples of the optionally halogeno alkoxy group are 2,2,2-trifluoroethoxy, 2,2,3,3,3-pentafluoropropoxy, 1-(trifluoromethyl)-2,2,2-trifluoroethoxy, 2,2,3,3-tetrafluoropropoxy, 2,2,3,3,4,4,4-heptafluorobutoxy, 2,2,3,3,4,4,5,5-octafluoropentoxy, methoxy, and the like. The optionally halogeno alkoxyalkoxy group is preferably 3-methoxypropoxy.

The preferred, among the compounds of the formula (I), are (1) compounds wherein ring A is either unsubstituted or substituted by methoxy or trifluoromethyl; R3 is hydrogen; R5 and R7 are, the same or different, hydrogen or methyl; R6 is a C 1–5 alkoxy which may be fluorinated; R8 is hydrogen; and X is S, SO or SO$_2$, (2) compounds wherein ring A is unsubstituted or substituted by fluorine, methoxy or trifluoromethyl; R3 is hydrogen; R5 is hydrogen or methoxy; R6 is a C 3–8 alkoxy group; both of R7 and R8 are hydrogens; and X is SO, and (3) compounds wherein ring A is unsubstituted or substituted by fluorine, methoxy or trifluoromethyl; R3 is hydrogen; R5 is a C 1–6 alkoxy group; R6 is a C 1–8 alkoxy group which may be fluorinated; both of R7 and R8 are hydrogens; and X is SO.

Illustrative compounds according to the invention are:

4-trifluoromethyl-2-[(4-methoxy-2-pyridylmethyl)thiol]-(1H)-benzimidazole, 4-trifluoromethyl-2-[(4-methoxy-3-methyl-2-pyridylmethyl)thio]-(1H)-benzimidazole, 4-trifluoromethyl-2-[(4-methoxy-5-methyl-2-pyridylmethyl)thio]-(1H)-benzimidazole, 4-trifluoromethyl-2-[(4-methoxy-3,5-dimethyl-2-pyridylmethyl)thio]-(1H)-benzimidazole, 5-trifluoromethyl-2-[(4-methoxy-2-pyridylmethyl)thio]-(1H)-benzimidazole, 5-trifluoromethyl-2-[(4-methoxy-3-methyl-2-pyridylmethyl)thio]-(1H)-benzimidazole, 5-trifluoromethyl-2-[(4-methoxy-5-methyl-2-pyridylmethyl)thio]-(1H)-benzimidazole, 5-trifluoromethyl-2-[(4-methoxy-3,5-dimethyl-2-pyridylmethyl)thio]-(1H)-benzimidazole, 4-trifluoromethyl-2-[(4-methoxy-2-pyridylmethyl)-sulfinyl]-(1H)-benzimidazole, 4-trifluoromethyl-2-[(4-methoxy-3-methyl-2-pyridylmethyl)sulfinyl]-(1H)-benzimidazole, 4-trifluoromethyl-2-[(4-methoxy-5-methyl-2-pyridylmethyl)sulfinyl]-(1H)-benzimidazole, 4-trifluoromethyl-2-[(4-methoxy-3,5-dimethyl-2-pyridylmethyl)sulfinyl]-(1H)-benzimidazole, 5-trifluoromethyl-2-[(4-methoxy-2-pyridylmethyl)sulfinyl]-(1H)-benzimidazole, 5-trifluoromethyl-2-[(4-methoxy-3-methyl-2-pyridylmethyl)sulfinyl]-(1H)-benzimidazole, 5-trifluoromethyl-2-[(4-methoxy-5-methyl-2-pyridylmethyl)sulfinyl]-(1H)-benzimidazole and 5-trifluoromethyl-2-[(4-methoxy-3,5-dimethyl-2-pyridylmethyl)sulfinyl]-(1H)-benzimidazole, 2-[2-(4-methoxy)-pyridylmethylsulfinyl]-(5-acetyl-6-methyl)-benzimidazole, 2-[2-(4-methoxy)-pyridylmethylsulfinyl]-(4,6-dimethyl)-benzimidazole, 2-[2-(3,5-dimethyl-4-methoxy)-pyridylmethylsulfinyl]-(5-acetyl-6-methyl)-benzimidazole, 2-[2-(4-methoxy)-pyridylmethylsulfinyl]-(5-carbomethoxy-6-methyl)-benzimidazole, 2-[2-(4-ethoxy)-pyridylmethylsulfinyl]-(5-carbomethoxy-6-methyl)-benzimidazole, 2-[2-(3-methyl-4-methoxy)-pyridylmethylsulfinyl]-(5-carbomethoxy-6-methyl)-benzimidazole, 2-[2-(3,5-dimethyl-4-methoxy)-pyridylmethylsulfinyl]-(5-carbomethoxy-6-methyl)-benzimidazole, 2-[2-(4-methoxy-5-methyl)-pyridylmethylsulfinyl]-(5-carbomethoxy)-benzimidazole, 2-[2-(3,5-dimethyl-4-methoxy)-pyridylmethylsulfinyl]-5-carbomethoxy-benzimidazole, 2-[2-(3,5-dimethyl-4-methoxy)-pyridylmethylsulfinyl]-(5-acetyl)-benzimidazole, 2-[2-(4-methoxy-5-methoxy)-pyridylmethylsulfinyl]-(5-methoxy)-benzimidazole, 2-[2-(3,5-dimethyl-4-methoxy)-pyridylmethylsulfinyl]-(5-methoxy)-benzimidazole, 2-[2-(3,5-dimethyl-4-methoxy)-pyridylmethylsulfinyl]-(5-methyl)-benzimidazole, 2-[2-(3,5-dimethyl-4-methoxy)-pyrdylmethysulfinyl]-benzimidazole, 2-[2-(3,5-dimethyl-4-methoxy)-pyridylmethylsulfinyl]-(5-chloro)-benzimidazole 2-[2-[3-methyl-4-(2,2,2-trifluoroethoxy)pyridyl]methylsulfinyl]benzimidazole(lansoprazole), 2-[2-[3-methyl-4-(2,2,3,3-tetrafluoropropoxy)pyridyl]methylthio]benzimidazole, 2-[(2-pyridyl)methylsulfinyl]benzimidazole (thimoprazole), 2-[2-(3,5-dimethyl-4-methoxypyridyl)methylsulfinyl]-5-methoxy-1H-benzimidazole (omeprazole), 2-[2-[4-(3-methoxypropoxy)-3-methylpyridyl]methylsulfinyl]-1H-benzimidazole, 2-[2-(3,4-dimethoxypyridyl)methylsulfinyl]-5-difluoromethoxy-1 H-benzimidazole (pantoprazole), 4-methyl-3-(2,2,2-trifluoroethoxy)-5H-pyrido[1',2':4,5][1,2,4]thiaziano[2,3-a] benzimidazol-13-ium tetrafluoroborate or a pharmaceutically acceptable salt thereof in a therapeutically effective amount is administered for activation of lung epithelial cell chloride channels.

The benzimidazole compounds can be used in the form of a physiologically acceptable salt. The physiologically acceptable salt includes salts with inorganic bases, salts with organic bases, and salts with basic amino acids. Among the inorganic bases mentioned above are alkali metals (e.g. sodium, potassium, etc.) and alkaline earth metals (e.g. calcium, magnesium, etc.). The organic bases may be trimethylamine, triethylamine, pyridine, picoline, N,N-dibenzylethylenediamine, ethanolamine, diethanolamine, trishydroxymethylaminomethane, dicyclohexylamine, etc. The basic amino acids may be arginine, lysine and so on.

These salts can be produced by the per se known production processes, for example the processes described in EP-A-295603 and U.S. Pat. No. 4,738,974 or any processes analogous therewith.

Depending on the process conditions and the starting materials, the end product obtained in production of the product is either as the free base or in the acid addition salt, both of which are included within the scope of the invention. Thus, basic, neutral or or mixed salts may be obtained as well as hemi, mono, sesqui or polyhydrates. The acid addition salts of the new compounds may in a manner known per se be transformed into free base using basic agents such as alkali or by ion exchange. On the other hand, the free bases obtained may form salts with organic or inorganic acids. In the preparation of acid addition salts preferably such acids are used which form suitable therapeutically acceptable salts. Such acids include hydrohalogen acids, sulfoni, phosphoric, nitric, and perchloric acids; aliphatic, alicyclic, aromatic, heterocyclic carboxy or sulfonic acids, such as formic, acetic, propionic, succinic, glycolic, lactic, malic, tartaric, citric, ascorbic, maleic, hydroxymaleic, pyruvic, phenylacetic, benzoic, p-aminobenzoic, antranilic, p-hydroxybenzoic, salicylic or p-aminosalicylic acid, embonic, methanesulfonic, ethanesulfonic, hydroxyethanesulfonic, ethylenesulfonic, halogenbenzenesulfonic, toluenesulfonic, naphtylsulfonic or sulfanilic acids; methionine, tryptophane, lysine or arginine.

Epithelial cells treated with these compounds show increased transport of some ions including chloride, consistent with the view that these compounds transport anions across biological membranes without obvious acute damage to biological membranes.

Without wishing to be bound by theory, omeprazole is thought to form reactive species upon acid activation in the lung environment. The active omeprazole then reacts with sulfhydryl groups of proteins. The omeprazole can then be used to treat cystic fibrosis by treatment of lung epithelia by sprays, inhalation, or lavage with this compound.

It is contemplated that such target cells may be located within an animal or human patient, in which case a safe and effective amount of the complex, in pharmacologically acceptable form, would be administered to the patient. Generally speaking, it is contemplated that useful pharmaceutical compositions of the present invention will include the selected benzimidazole derivative in a convenient amount, e.g., from about 0.001% to about 10% (w/w) that is diluted in a pharmacologically or physiologically acceptable carrier, such as, for example, phosphate buffered saline. The route of administration and ultimate amount of material that is administered to the patient or animal under such circumstances will depend upon the intended application and will be apparent to those of skill in the art in light of the examples which follow.

Any composition chosen should be of low or non-toxicity to the cell. Toxicity for any given compound may vary with the concentration of compound used. It is also beneficial if the compound chosen is metabolized or eliminated by the body and if this metabolism or elimination is done in a manner that will not be harmfully toxic.

The examples are illustrative of the types of compounds to be used in the method claimed herein; the list is not exhaustive. Derivatives of the above compounds which fit the criteria of the claims should also be considered when choosing a benzimidazole compound.

The composition can comprise, in addition to one or more benzimidazole compounds, compounds and/or compositions that will also aid in relief of the symptoms of cystic fibrosis, such as a cyclic AMP agonist, a calcium ion agonist, human DNase 1, a sodium channel blocker or a pancreatic enzyme supplement, in dosages useful for relief of the symptoms of cystic fibrosis, as known to those skilled in the art. Cyclic AMP agonists can include, for example, forskolin and isoproterenol. Calcium ion agonists can include ionomycin, A23 187, carbachol, bradykinin, duramycin and thapsigargin, for example. Sodium channel blockers can include amiloride and triamterene. Dosages for the above-mentioned additional compounds are established and known to those skilled in the art (see, e.g., Knowles et al., *New Eng. J. Med.* 322:1189–1194 (1990)).

Compositions for treating cystic fibrosis are provided which comprise a combination of a safe and effective amount of a suitable benzimidazole compound as described above, a pharmaceutically-acceptable carrier, and a safe and effective amount of an agent selected from the group consisting of human DNase I, cystic fibrosis transmembrane conductance regulator protein or a biologically active portion thereof, nucleic acid encoding functional cystic fibrosis transmembrane conductance regulator protein, a cyclic AMP agonist, a calcium agonist, a sodium channel blocker and a pancreatic enzyme supplement, as also described above. More than one agent can be added to the benzimidazole compound. The ratio of benzimidazole compound to additional agent is dependent upon the dose desired of each individual compound. Preferably, the additional agent will be administered as a pharmaceutically acceptable aqueous solution wherein the pharmaceutical composition comprises (1) from about 0.001% to about 90% of a benzimidazole derivative, (2) from about 10% to about 99.9% of a pharmaceutically-acceptable carrier, and (3) from about 0.001% to about 10% of the additional agent or agents as described above.

The compound useful in the present inventive method may be administered by any suitable means. One skilled in the art will appreciate that many suitable methods of administering the compound to an animal in the context of the present invention, in particular a human, are available, and, although more than one route may be used to administer a particular compound, a particular route of administration may provide a more immediate and more effective reaction than another route.

The compound may be administered directly to the lung of a patient. Preferably, the compound is administered as a pharmaceutically acceptable aqueous solution or suspension. It is preferable that the compound be administered as a pharmaceutically acceptable aqueous solution containing from about 0.001% to about 90% (w/w) of the compound. A pharmaceutically acceptable aerosol is another preferred means of administration. The aerosol preferably contains from about 0.001% to about 90% (w/w) of the compound. The compound also may be administered orally. In such cases, the compound will generally be administered in an amount of about 0.01 to about 10 mg/kg body weight. Other routes of administration, such as intravenous and intraperitoneal administration, are also possible.

The compound should be administered such that a therapeutically effective concentration of the compound is in contact with the affected cells of the body. The dose administered to an animal, particularly a human, in the context of the present invention should be sufficient to effect a therapeutic response in the animal over a reasonable period of time. The dose will be determined by the strength of the particular compound employed and the condition of the animal, as well as the body weight of the animal to be treated. The size of the dose also will be determined by the existence, nature, and extent of any adverse side effects that might accompany the administration of a particular compound and the particular route of administration employed with a particular patient. In general, the compounds of the present invention are therapeutically effective at low doses. The effective dose range is from about 0.01 mM to about 10 mM. Accordingly, the compounds will be generally administered in low doses.

The compound may be administered in a pharmaceutically acceptable carrier. Pharmaceutically acceptable carriers are well-known to those who are skilled in the art. The choice of carrier will be determined in part by the particular compound, as well as by the particular method used to administer the composition. Accordingly, there is a wide variety of suitable formulations of the pharmaceutical composition of the present invention.

Formulations suitable for oral administration include (a) liquid solutions, such as an effective amount of the compound dissolved in diluents, such as water or saline, (b) capsules, sachets or tablets, each containing a predetermined amount of the active ingredient, as solids or granules, (c) suspensions in an appropriate liquid, and (d) suitable emulsions. Tablet forms may include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels and the like containing, in addition to the active ingredient, such carriers as are known in the art.

Formulations suitable for administration by inhalation include aerosol formulations placed into pressurized acceptable propellants, such as dichlorodifluoromethane, propane, nitrogen, and the like. The active agent may be aerosolized with suitable excipients. For inhalation administration, the composition can be dissolved or dispersed in liquid form, such as in water or saline, preferably at a concentration at which the composition is fully solubilized and at which a suitable dose can be administered within an inhalable volume. A suitable dose would place approximately 0.001 to about 5.0 mmol per liter of the composition on the airway surfaces approximately 4 times per day. Delivery can be repeated several times a day, depending upon the specific dosage chosen and the rate at which the chosen composition is cleared from the airways, with the goal being to maintain chloride permeability in the airway epithelial cells.

Formulations suitable for intravenous and intraperitoneal administration, for example, include aqueous and nonaqueous, isotonic sterile injection solutions, which can contain anti-oxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carriers for example, water, for injections, immediately prior to use. Extemporaneous injection solutions and suspensions can be prepared for sterile powders, granules, and tablets of the kind previously described.

Parenteral administration, if used, could also be by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795, Higuchi, issued 1973, which is incorporated by reference herein.

The desirable extent of the induction of chloride efflux from cells will depend on the particular condition or disease being treated, as well as the stability of the patient and possible side effects. In proper doses and with suitable administration of certain compounds, the present invention provides for a wide range of activation of the rate of chloride ion efflux, e.g., from little activation to essentially full activation.

The present invention Is expected to be effective in the treatment of all conditions, including diseases, that may be characterized by a reduced cellular apical chloride conductance. In particular, the present invention is expected to have utility in the treatment of chronic obstructive pulmonary diseases, in particular cystic fibrosis.

The exact amount of such compounds required will vary from subject to subject, depending on the species, age, and general condition of the subject, the severity of the disease that is being treated, the particular compound used, its mode of administration, and the like. Thus, it is not possible to specify an exact activity promoting amount. However, an appropriate amount may be determined by one of ordinary skill in the art using only routine testing given the teachings herein.

What is claimed is:

1. A method for treating conditions which include as a symptom reduced permeability of chloride ions in cells comprising the administration to a person in need of such treatment of a safe and effective amount of a pharmaceutical composition comprising:

(a) from about 0.001% to about 90% (w/w) of a benzimidazole derivative having the formula (I):

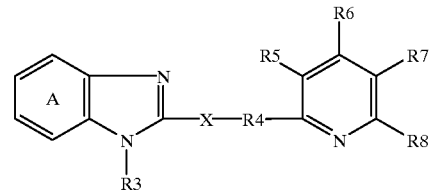

wherein ring A is substituted with one or more substituents selected from the group consisting of hydrogen, chloro, methyl, ethyl, acetyl, methoxy, carbethoxy, and carbomethoxy; R3 is selected from the group consisting of hydrogen, methyl, ethyl, n-propyl, iso-propyl, n-butyl, iso-butyl, sec-butyl and t-butyl; R4 is selected from the group consisting of straight and branched alkylene groups having one to four carbon atoms; R5 is selected from hydrogen, alkyl and alkoxy; R7 is selected from hydrogen, alkyl and alkoxy; R8 is hydrogen; R6 is hydrogen, chloro, methyl, ethyl, acetyl; methoxy, carbethoxy and carbomethoxy; and X is SO; and (b) from about 10% to about 99.999% of a pharmaceutically-acceptable carrier.

2. A method according to claim 1, wherein R6 is methoxy.

3. A method according to claim 1, wherein R3 is selected from the group consisting of hydrogen, methyl, or ethyl.

4. A method according to claim 1, wherein R4 is selected from the group consisting of methyl, ethyl, n-propyl, isopropyl, n-butyl, isobutyl, sec-butyl, and tert-butyl.

5. A method according to claim 1, wherein R4 is a methyl group.

6. A method according to claim 1, wherein R5 is selected from the group consisting of hydrogen and methyl.

7. A method according to claim 1, wherein R7 is selected from the group consisting of hydrogen and methyl.

8. A method according to claim 1, wherein the compound of formula I is selected from the group consisting of omeprazole, lansoprazole, thimoprazole, pantoprazole and pharmaceutically acceptable salts thereof.

9. A method according to claim 1, wherein the compound of formula I is omeprazole.

10. A method for treating conditions which include as a symptom reduced permeability of chloride ions in cells, comprising the administration to a person in need of such treatment of a safe and effective amount of a pharmaceutical composition comprising:

(a) from about 0.001% to about 90% (w/w) of a benzimidazole derivative selected from the group consisting of 4-trifluoromethyl-2-[(4-methoxy-2-pyridylmethyl)thiol]-(1H)-benzimidazole, 4-trifluoromethyl-2-[(4-methoxy-3-methyl-2-pyridylmethyl)thio]-(1H)-benzimidazole, 4-trifluoromethyl-2-[(4-methoxy-5-methyl-2-pyridylmethyl)thio]-(1H)-benzimidazole, 4-trifluoromethyl-2-[(4-methoxy-3,5-dimethyl-2-pyridylmethyl)thio]-(1H)-benzimidazole, 5-trifluoromethyl-2-[(4-methoxy-2-pyridylmethyl)thio]-(1H)-benzimidazole, 5-trifluoromethyl-2-[(4-methoxy-3-methyl-2-pyridylmethyl)thio]-(1H)-benzimidazole, 5-trifluoromethyl-2-[(4-methoxy-5-methyl-2-pyridylmethyl)thio]-(1H)-benzimidazole, 5-trifluoromethyl-2-[(4-methoxy-3,5-dimethyl-2-pyridylmethyl)thio]-(1H)-benzimidazole, 4-trifluoromethyl-2-[(4-methoxy-2-pyridylmethyl)-sulfinyl]-(1H)-benzimidazole, 4-trifluoromethyl-2-[(4-methoxy-3-methyl-2-pyridylmethyl)sulfinyl]-(1H)-benzimidazole, 4-trifluoromethyl-2-[(4-methoxy-5-methyl-2-pyridylmethyl)sulfinyl]-(1H)-benzimidazole, 4-trifluoromethyl-2-[(4-methoxy-3,5-dimethyl-2-pyridylmethyl)sulfinyl]-(1H)-benzimidazole, 5-trifluoromethyl-2-[(4-methoxy-2-pyridylmethyl)sulfinyl]-(1H)-benzimidazole, 5-trifluoromethyl-2-[(4-methoxy-3-methyl-2-pyridylmethyl)sulfinyl]-(1H)-benzimidazole, 5-trifluoromethyl-2-[(4-methoxy-5-methyl-2-pyridylmethyl)sulfinyl]-(1H)-benzimidazole and 5-trifluoromethyl-2-[(4-methoxy-3,5-dimethyl-2-pyridylmethyl)sulfinyl]-(1H)-benzimidazole, 2-[2-(4-methoxy)-pyridylmethylsulfinyl]-(5-acetyl-6-methyl)-benzimidazole, 2-[2-(4-methoxy)-pyridylmethylsulfinyl]-(4,6-dimethyl)-benzimidazole, 2-[2-(3,5-dimethyl-4-methoxy)-pyridylmethylsulfinyl]-(5-acetyl-6-methyl)-benzimidazole, 2-[2-(4-methoxy)-pyridylmethylsulfinyl]-(5-carbomethoxy-6-methyl)-benzimidazole, 2-[2-(4-ethoxy)-pyridylmethylsulfinyl]-(5-carbomethoxy-6-methyl)-benzimidazole, 2-[2-(3-methyl-4-methoxy)-pyridylmethylsulfinyl]-(5-carbomethoxy-6-methyl)-benzimidazole, 2-[2-(3,5-dimethyl-4-methoxy)-pyridylmethylsulfinyl]-(5-carbomethoxy-6-methyl)-benzimidazole, 2-[2-(4-methoxy-5-methyl)-pyridylmethylsulfinyl]-(5-carbomethoxy)-benzimidazole, 2-[2-(3,5-dimethyl-4-methoxy)-pyridylmethylsulfinyl]-5-carbomethoxy)-benzimidazole, 2-[2-(3,5-dimethyl-4-methoxy)-pyridylmethylsulfinyl]-(5-acetyl)-benzimidazole, 2-[2-(4-methoxy-5-methoxy)-pyridylmethylsulfinyl]-(5-methoxy)-benzimidazole, 2-[2-(3,5-dimethyl-4-methoxy)-pyridylmethylsulfinyl]-(5-methoxy)-benzimidazole, 2-[2-(3,5-dimethyl-4-methoxy)-pyridylmethylsulfinyl]-(5-methyl)-benzimidazole, 2-[2-(3,5-dimethyl-4-methoxy)-pyridylmethylsulfinyl]-benzimidazole, 2-[2-(3,5-dimethyl-4-methoxy)-pyridylmethylsulfinyl]-(5-chloro)-benzimidazole 2-[2-[3-methyl-4-(2,2,2-trifluoroethoxy)pyridyl]methylsulfinyl]benzimidazole(lansoprazole), 2-[2-[3-methyl-4-(2,2,3,3-tetrafluoropropoxy)pyridyl]methylthio]benzimidazole, 2-[(2-pyridyl)methylsulfinyl]benzimidazole (thimoprazole), 2-[2-(3,5-dimethyl-4-methoxypyridyl)methylsulfinyl]-5-methoxy-1H-benzimidazole (omeprazole), 2-[2-[4-(3-methoxypropoxy)-3-methylpyridyl]methylsulfinyl]-1H-benzimidazole, 2-[2-(3,4-dimethoxypyridyl)methylsulfinyl]-5-difluoromethoxy-1H-benzimidazole (pantoprazole), 4-methyl-3-(2,2,2-trifluoroethoxy)-5H-pyrido[1',2':4,5][1,2,4]thiaziano[2,3-a] benzimidazol-13-ium tetrafluoroborate, pharmaceutically acceptable salts thereof and mixtures thereof; and (b) from about 10% to about 99.999% of a pharmaceutically-acceptable carrier.

11. A pharmaceutical composition for treating conditions which include as a symptom reduced permeability of chloride ions in cells comprising:

(a) from about 0.001% to about 90% (w/w) of a benzimidazole having the formula (I):

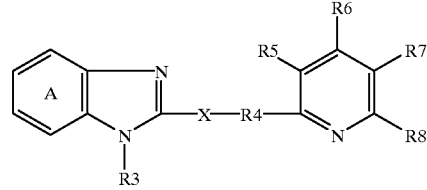

wherein ring A is substituted with one or more substituents selected from the group consisting of hydrogen, chloro, methyl, ethyl, acetyl, methoxy, carbethoxy, and carbomethoxy; R3 is selected from the group consisting of hydrogen, methyl, ethyl, n-propyl, iso-propyl, n-butyl, iso-butyl, sec-butyl and t-butyl; R4 is selected from the group consisting of straight and branched alkylene groups having one to four carbon atoms; R5 is selected from hydrogen, alkyl and alkoxy; R7 is selected from hydrogen, alkyl and alkoxy; R8 is hydrogen; R6 is hydrogen, chloro, methyl, ethyl, acetyl, methoxy, carbethoxy and carbomethoxy; and X is SO;

(b) from about 10% to about 99.999% of a pharmaceutically-acceptable carrier; and (c) from about 0.001% to about 10% (w/w) of an agent selected from the group consisting of amiloride, human DNase I, cystic fibrosis transmembrane conductance regulator protein or a biologically active portion thereof, nucleic acid encoding functional cystic fibrosis transmembrane conductance regulator protein, a cyclic AMP agonist, a calcium ion agonist, a pancreatic enzyme supplement and mixtures thereof.

* * * * *